United States Patent [19]

Ishida et al.

[11] Patent Number: 4,885,245

[45] Date of Patent: Dec. 5, 1989

[54] PROCESS FOR PRODUCING L-TRYPTOPHAN

[75] Inventors: Masaaki Ishida, Kawasaki; Kiyoshi Miwa, Matsudo; Shigeru Nakamori, Yokohama; Konosuke Sano, Tokyo, all of Japan

[73] Assignee: Ajinomoto Co., Inc., Tokyo, Japan

[21] Appl. No.: 760,930

[22] Filed: Jul. 31, 1985

[30] Foreign Application Priority Data

Jul. 31, 1984 [JP] Japan ................................. 59-161217

[51] Int. Cl.⁴ ............................................. C12N 15/00
[52] U.S. Cl. ............................... 435/108; 435/252.32; 435/320; 435/172.3; 935/23; 935/27
[58] Field of Search ...................... 435/108, 252, 172.3; 935/56

[56] References Cited

U.S. PATENT DOCUMENTS 3,700,559  10/1972  Shiio ..................................... 435/108
4,360,594  11/1982  Mimura ................................. 435/108
4,617,267  10/1986  Katsumata ........................... 435/253

OTHER PUBLICATIONS

Herrmann et al, Amino Acids Biosynthesis and Genetic Regulation (1983), pp. 351–375.
Aiba et al., Appl. and Env. Microbiol., 43(2)(1982), pp. 289–297.

*Primary Examiner*—T. G. Wiseman
*Assistant Examiner*—Patricia Carson
*Attorney, Agent, or Firm*—Oblon, Spivak, McClelland, Maier & Neustadt

[57] ABSTRACT

A process for producing L-tryptophan in which a suitable substrate such as a carbohydrate, indole or anthranilic acid is contacted with Coryneform bacteria, where the Coryneform bacteria bear recombinant DNA constructed by connecting a gene coding for tryptophan synthetase with a plasmid vector capable of proliferating in Coryneform bacteria.

9 Claims, No Drawings

PROCESS FOR PRODUCING L-TRYPTOPHAN

BACKGROUND OF THE INVENTION

1. Field of the Invention

The present invention relates to a process for producing L-tryptophan using Coryneform bacteria which have been constructed by a recombinant DNA technique.

2. Description of the Related Art

In a process for producing L-tryptophan using microorganisms, where it is attempted to produce L-tryptophan using carbohydrates such as glucose or the like as raw materials, wild strains do not produce L-Tryptophan outside of cells and thus, there is known a process which comprises artifically causing mutation of wild strains in order to impart L-tryptophan productivity ot the wild strains.

As hitherto known mutants having L-tryptophan productivity, there are known mutants of the genus Brevibacterium, Microbacterium or Corynebacterium which are resistant to 5-methyltryptophan (U.S. Pat. No. 3,700,559); mutants of the genus Corynebacterium which require tyrosine and phenylalanine and are resistant to phenylalanine antogonists (Published Examined Japanese Patent Application No. 10937/76); mutants of the genus Bacillus which are resistant to 5-fluorotryptophan (published Unexamined Japanese Patent Application No. 85289/74); mutants of the genus Brevibacterium which are resistant to 5-methyltryptophan and m-fluorotryptophan (Published Unexamined Japanese Patent Application No. 42091/75); and others.

On the other hand, some attempts to utilize recombinant DNA techniques different from the abovementioned breeding involving mutations have also been reported recently. For example, in Appl. Environ. Microbiol., 38 (2), 181–190 (1979), it is described that a particular mutant of *Escherichia coli* containing a plasmid bearing a trp E472 gene of *Escherichia coli* produces approximately 1.3 g/l of L-tryptophan. Further, it is mentioned in "Fermentation Technology Association, Japan, Summary of Lectures in the 1980th Conference," page 170 (1980) that a mutant of *Escherichia coli* containing a plasmid having incorporated therein the tryptophan operon of *Escherichia coli* produced 360 mg/l of L-tryptophan.

Furthermore, it is mentioned in Published Unexamined Japanese Patent Application No. 208994/82 that L-tryptophan is produced using a microorganism belonging to the genus Bacillus which is constructed by a recombinant DNA technique.

On the other hand, many processes for producing L-tryptophan using anthranilic acid or indole as a raw material are know (for example, Published Examined Japanese Patent Application Nos. 16955/71, 46348/72 and 29584/82, Published Unexamined Japanese Patent Application Nos. 00785/73, 87085/73 and 95484/75, etc.)

Further, there is also known a process for producing L-tryptophan from indole or anthranilic acid using bacteria belonging to the genus Bacillus by a recombinant DNA technique (Published Unexamined Japanese Patent Application No. 89194/73).

SUMMARY OF THE INVENTION

Accordingly, an object of the present invention is to provide a process for producing L-tryptophan more effectively and in higher yields than in the prior art processes.

It is another object of this invention to describe production of Coryneform bacteria containing recombinant DNA which are capable of producing L-tryptophan from carbohydrates, arthranilic acid or indole.

DESCRIPTION OF THE PREFERRED EMBODIMENTS

The present inventors have succeeded in obtaining Coryneform bacteria bearing recombinant DNAs constructed by connecting a gene coding for tryptophan synthetase (4.2.1.20, hereafter referred to as "TS") with a plasmid vector capable of proliferating in the Coryneform bacteria and have succeeded in developing a process for producing L-tryptophan effectively from carbohydrates, anthranilic acid or indole using such Coryneform bacteria.

The Coryneform bacteria as used in the present invention are aerobic, non-acid fast, gram-positive bacilli which are described in Bergey's Manual of Determinative Bacteriology, 8th Edition, page 599 (1974). Of these, the bacteria shown below are known as those that produce L-tryptophan in large quantities. It is believed that these bacteria all belong to the same genus.

*Brevibacterium divaricatum* ATCC 14020
*Brevibacterium saccarolyticum* ATCC 14066
*Brevibacterium immariophilum* ATCC 14068
*Brevibacterium lactofermentum* ATCC 13869
*Brevibacterium roseum* ATCC 13825
*Brevibacterium flavum* ATCC 13826
*Brevibacterium thiogenitalis* ATCC 19240
*Corynebacterium acetoacidophilum* ATCC 13870
*Corynebacterium acetoglutamicum* ATCC 15806
*Corynebacterium callunae* ATCC 15991
*Corynebacterium glutamicum* ATCC 13032, 13060
*Corynebacterium lilium* ATCC 15990
*Corynebacterium melassecola* ATCC 17965
*Microbacterium ammoniaphilum* ATCC 15354.

In addition to the Coryneform bacteria having a L-tryptophan productivity as described above, Coryneform bacteria also include variants which lose the L-tryptophan productivity and other variants.

A method for isolating the TS gene comprises first extracting chromosomal DNA containing the TS gene from Coryneform bacteria (techniques described, for example, in H. Saito and K. Miura, Biochem. Biophys. Acta, 72, 619 (1963), etc. can be used), cleaving the DNA with a suitable restriction enzyme; then, inserting the cleaved DNA into a plasmid vector capable of proliferating in Coryneform bacteria; transforming TS-deficient variants of Coryneform bacteria using the obtained recombinant DNA; isolating resulting bacteria which possess TS productivity; and isolating the plasmid possessing the TS gene.

A wide variety of restriction enzymes can be used for cleaving the chromosomal gene by controlling the degree of cleavage through controlling the reaction time for the cleavage.

Any plasmid vector can be utilized in the present invention, as long as it is capable of proliferating in Coryneform bacterial cells. Specific examples are shown below.

(1) pAM 330—cf. Published Unexamined Japanese Patent Application No. 67699/83
(2) pAM 1519—cf. Published Unexamined Japanese Patent Application No. 77895/83

(3) pAJ 655—cf. Published Unexamined Japanese Patent Application No. 216199/83
(4) pAJ 611—same as above
(5) pAJ 1844—same as above
(6) pCG 1—cf. Published Unexamined Japanese Patent Application No. 134500/82
(7) pCG 2—cf. Published Unexamined Japanese Patent Application No. 35197/83
(8) pCG 4—cf. Published Unexamined Japanese Patent Application No. 183799/82
(9) pCG 11—same as above The vector DNA is digested with the same restriction enzyme as that used for digestion of the chromosomal DNA or they are digested with different enzymes, then connected to oligonucleotides having complementary base sequences at both termini of the chromosomal DNA and vector DNA fragments, and the vector and chromosomal DNA fragments are then subjected to a ligation reaction.

To introduce the thus obtained recombinant DNA made up of the chromosomal DNA and plasmid DNA into recipient bacteria belonging to Coryneform bacteria, a process may be employed which comprises treating recipient cells with calcium chloride to increase the permeability of DNA as reported for *Escherichia coli* K-12 (Mandel, M. and Higa, A., J. Mol. Biol., 53, 159 (1970)); alternatively, a process may be employed which comprises introducing recombinant DNA into the exponentially growing cells (so-called competent cells) as reported for *Bacillus subtilis* (Duncan, D. H., Wilson, G. A. and Young, F. E., Gene, 1, 153 (1977)); or this second process may be carried out in a manner known with respect to Actinomyces and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. U.S.A., 75, 1939 (1978)). It is also possible to change the recipient cells into protoplasts or spheroplasts which allow easy introduction of environmental DNA fragments.

In the protoplast or spherophast technique, sufficiently high frequency can be obtained even by the above-described process used for *Bacillus subtilis* (Chang and Cohen). Of course, the process which comprises allowing DNA to become incorporated into protoplasts of the genus Corynebacterium or the genus Brevibacterium described in Published Unexamined Japanese Patent Application No. 183799/82 in the presence of polyethylene glycol or polyvinly alcohol and divalent metal ions, can also be utilized. By a process in which incorporation of DNA is accelerated by the addition of carboxymethyl cellulose, dextran, phycoll, Pluronic F 68 (Serva Co., Ltd.), etc. in place of polyethylene glycol or polyvinyl alcohol, similar results can also be obtained.

After transformation, strains which have acquired TS-activity and which express a marker gene on the vectors are obtained as transformants. Such transformants have recombinant DNA containing TS genes. To isolate the recombinant DNA, the transformed cells are lysed, for example, by a treatment with lysozyme and SDS, treated with phenol to denature proteins, then 2 volumes of ethanol are added thereto to precipitate and recover DNA.

The process for producing L-tryptophan using the thus obtained Coryneform bacteria bearing the recombinant DNA may be roughly classified into one of three groups depending upon the raw materials employed in the process. However, this classification scheme is referred to only for the purpose of making the invention understood more easily and, in practice, it may often be unclear as to which group a particular process may be classified.

The first case is to produce L-tryptophan using carbohydrates as raw materials. Namely, as a medium an ordinary medium containing carbohydrates as a carbon source, nitrogen sources, inorganic ions and, if necessary, further containing organic trace nutrients such as amino acids, vitamins, etc., may be used. As the carbohydrates, glucose, sucrose, fructose, lactose, etc., and starch hydrolysates, whey, molasses, etc., may be used. As the nitrogen source, ammonia gas, ammonia water, ammonium salts and others may be employed.

Cultivation is carried out generally for 2 to 4 days until the production and accumulation of L-tryptophan are substantially finished, while appropriately controlling the pH of the medium and temperature under aerobic conditions. Thus, marked amounts of L-tryptophan are produced and accumulated in the medium.

The second case is where indole or anthranilic acid is added to the medium as used in the first case at the time of instruction of cultivation, or to the medium during cultivation. This case is similar to the first one in that L-tryptophan is produced under conditions where Coryneform bacteria bearing the recombinant DNA can propagate, but indole is used as a raw material for producing L-tryptophan.

Anthranilic acid or indole may be incorporated into the medium from the outset of cultivation or may be incorporated into the medium during cultivation, particularly after Coryneform bacteria grow sufficiently so as not to prevent propagation by the additives. It is desired that the amount of anthranilic acid or indole to be incorporated in the medium be such that the amount does not exceed a concentration in the medium which inhibits the propagation of Coryneform bacteria. For this reason, small quantities of anthranilic acid or indole may be added to the medium continuously or by dividing the amount into several additions at different times. On some occasions, further addition of one or more ribose donors and alanine side chain donors described hereinafter to the medium may provide better results.

Cultivation of Coryneform bacteria is carried out by a method substantially the same as in the first case except for the points described above.

The third case is very similar to the second case in that anthranilic acid and indole are used as raw materials for producing L-tryptophan but is different from the first one in that L-tryptophan is produced under such conditions that the propagation of Coryneform bacteria is unnecessary or Coryneform bacteria do not propagate. Namely, the third case is different from the first and second cases in that the propagation of Coryneform bacteria and the production of L-tryptophan are substantially separately performed.

As a medium for propagating Coryneform bacteria, an ordinary medium containing carbon sources described hereinbefore, nitrogen sources, inorganic ions and, if necessary, further containing organic trace nutrients such as amino acids, vitamins, etc. may be used. The addition of anthranilic acid or indole in a small quantity to the medium may often provide bacteria having a higher L-tryptophan producing activity. It is preferred to perform cultivation under aerobic conditions, as described hereinbefore.

After cultivation, Coryneform bacterial cells are once separated. The bacterial cells may be used in the form of a culture broth as it is; alternativley, cells separated from the culture broth by filtration, centrifugation, etc., or cells washed with water, acetone, surface active agents, etc., may also be used. In addition, cells obtained by immobilizing, pulverizing or grinding the above-described bacterial cells, or proteinaceous fractions appropriately separated therefrom, and further products obtained by treating the bacterial cells such as separated TS proteins, etc., may also be employed.

These bacterial cells or treated products are added to an aqueous medium together with anthranilic acid or indole in order to produce L-tryptophan. It is advantageous that the bacterial cells or treated products be used in an amount of from 0.5 to 5 g/dl (dry basis) calculated as the amount of the cells. In a case where a culture broth per se is used as the source of bacterial cells, the culture broth may be used as it is or it may be diluted with water, etc. In a case where the bacterial cells once separated or treated products are used, phosphate buffer may be used or only water may be used.

Further addition of sodium sulfite, ethylenediamine tetraacetic acid, pyridoxal phosphate or organic solvent such as acetone, ethanol, etc., surface active agents, etc., to the suspension may often provide better results. Further, when inosine is added to aqueous medium, a substantially insoluble tryptophan-inosine complex is formed so that tryptophan is removed from the reaction solution and thus, the reaction tends to proceed more toward the production of L-tryptophan.

A preferred concentration of anthranilic acid or indole is 0.1 to 5 g/dl in the case of anthranilic acid and 0.1 to 4.5 g/dl in the case of indole.

When anthranilic acid is used as the raw material, a ribose donor selected from ribose, 5-phosphoribose, 1-phosphoribose and 5-phosphoribose pyrophosphate is added to the aqueous medium. It is preferred that the ribose donor be in an amount of from 0.1 to 5 g/dl in any case. When anthranilic acid is added as a substrate in a high concentration, it is desirable to accordingly increase the concentration of these additives.

When indole is used as the raw material, an alanine side chain donor or pyruvic acid and ammonium ions are added to the aqueous medium. The alanine side chain donor is represented by the following general formula:

wherein X is a hydroxyl group, a halogen, an alkylmercapto group, a mercapto group, an alkoxy group, a benzyloxy group or a thiobenzyl group.

As referred to in this application, alkylmercapto or alkoxy means a group having preferably one to six carbon atoms in the alkyl portion. Further, benzyl groups (benzyloxy or thiobenzyl) may be unsubstituted or substituted with hydroxyl, halogen or $C_1$–$C_6$ alkyl or alkoxy on the aromatic ring.

The amount of each of the alanine side chain donor and pyruvic acid is 0.1M to 1M. In the reaction for producing L-tryptophan, the aqueous medium may be shaken and reacted at 25° C. to 45° C. for 10 to 48 hours in the case of anthranilic acid. Further, in the case of indole, it is preferred that the aqueous medium be settled or reacted by mildly shaking at 25° C. to 45° C. for 5 to 48 hours.

The culture solution obtained by the first, second and third cases or L-tryptophan produced in the aqueous medium may be separated and harvested in a conventional manner.

The invention now being generally described, the same will be better understood by reference to certain specific examples which are included herein for purposes of illustration only and are not intended to be limiting of the invention or any embodiment thereof, unless specified.

EXAMPLES

EXAMPLE 1

(1) Preparation of chromosomal DNA containing TS gene:

*Brevibacterium lactofermentum* AJ 12030 FERM-BP 276 bearing the TS gene which was resistant to feedback inhibition by L-tryptophan was inoculated in 1 liter of CMG medium (which contained 1 g/dl of peptone, 1 g/dl of yeast extract, 0.5 g/dl of glucose and 0.5 g/dl of NaCl and had been adjusted to a pH of 7.2). Shake culture was conducted at 30° C. for about 3 hours and cells were harvested at logarithmic growth phase. After the cells were lysed with lysozyme and SDS, chromosomal DNA was extracted and purified by the conventional phenol method to finally obtain 3.5 mg of DNA.

(2) Preparation of vector DNA:

As a vector, pAJ 1844 (molecular weight, 5.4 megadaltons) was used. Its DNA was prepared as follows:

First, *Brevibacterium lactofermentum* AJ 12037 (FERM-P 7234 FERM-BP 577) having pAJ 1844 as a plasmid was inoculated in 100 ml of CMG medium. After culturing at 30° C. to reach late logarithmic growth phase, the cells were lysed by lysozyme and SDS. The supernatant was obtained by ultracentrifugation at 30,000×g for 30 minutes. After the treatment with phenol, 2 volumes of ethanol were added to recover DNA as a precipitate. After the DNA was dissolved in a small quantity of TEN buffer (20 mM tris hydrochloride, 20 mM NaCl, 1 mM EDTA 9, pH 8.0), the solution was subjected to agarose gel electrophoresis to separate the vector DNA and chromosomal DNA. Thereafter, the separated vector DNA was taken out to obtain about 12 μg of pAJ 1844 plasmid DNA.

(3) Insertion of chromosomal DNA fragment into vector DNA:

The chromosomal DNA, 20 μg, obtained in (1) and 10 μg of the plasmid DNA obtained in (2) were treated with restriction endonuclease Pst I at 37° C. for 30 minutes. After heat treatment at 65° C. for 10 minutes, the two reaction solutions were mixed with each other and, the mixture was subjected to a ligation reaction of DNA fragments with $T_4$ phage-derived DNA ligase at 10° C. for 24 hours in the presence of ATP and dithiothreitol. After heat treatment at 65° C. for 10 minutes, a 2-fold volume of ethanol was added to the reaction solution to precipitate and harvest DNA.

(4) Transformation

*Brevibacterium lactofermentum* No. 21 which is deficient in a gene for the α-subunit of TS (hereafter simply referred to as TSA) was used as the recipient cell.

As the transformation method, a protoplast transformation method was used. First, the cells were cultured in 5 ml of CMG liquid medium to reach an earlier logarithmic growth phase. After adding 0.6 unit/ml of penicillin, shake culture was conducted for an additional 1.5 hour. Cells were harvested by centrifugation and washed with 0.5 ml of SMMP medium (pH 6.5) composed of 0.5M sucrose, 20 mM maleic acid, 20 mM magnesium chloride and 3.5% Pennassay browth (Difco) and then suspended in SMMP medium containing 10 mg/ml of lysozyme. The suspension was treated at 30° C. for 20 hours to obtain protoplasts. After centrifuging at 6000×g for 10 minutes, the protoplasts were washed with SMMP and resuspended in 0.5 ml of SMMP. The thus obtained protoplasts were mixed with 10 μg of DNA prepared in (3) in the presence of 5 mM EDTA. After polyethylene glycol was added to the mixture to reach the final concentration of 30%, the mixture was allowed to stand at room temperature for 2 minutes to incorporate DNA into the protoplasts. After the protoplasts were washed with 1 ml of SMMP medium, they were resuspended in 1 ml of SMMP and the suspension was cultured at 30° C. for 2 hours for phenotypic expression. The culture solution was spread onto a protoplast regeneration medium of pH 7.0. The regeneration medium contained, per one liter of distilled water, 12 g of tris(hydroxymethyl)aminomethane, 0.5 g of KCl, 10 g of glucose, 8.1 g of $MgCl_2.6H_2O$, 2.2 g of $CaCl_2.2H_2O$, 4 g of peptone, 4 g of yeast extract powder, 1 g of Casamino Acid (Difco Co., Ltd.), 0.2 g of $K_2HPO_4$, 135 g of sodium succinate, 8 g of agar and 3 μg/ml of chloramphenicol.

After culturing at 30° C. for 2 weeks, about 10,000 colonies resistant to chloramphenicol appeared, which were replicated in threonine-free medium (Thr deficient medium) which contained 2% of glucose, 1% of ammonium sulfate, 0.25% of urea, 0.1% of dihydrogen potassium phosphate, 0.04% of magnesium sulfate heptahydrate, 1 mg/dl of $FeSO_4.7H_2O$, 1 mg/dl of $MnSO_4.4H_2O$, 200 μg/dl of thiamine hydrochloride and 50 μg/dl of biotin, pH 7.0, 1.8% of agar, and 3 strains which were resistant to chloramphenicol and tryptophan independent were obtained.

(5) Analysis of plasmid DNA of transformant

From the transformant, a lystate was prepared by the method described in (2). When plasmid DNA was detected by agarose gel electrophoresis, a plasmid obviously larger than the vector was detected. It was confirmed that the TSA gene was present on the recombinant plasmid in the transformant. This strain was named AJ 12140 (FERM-P 7749, FERM-BP 846) and the recombinant plasmid was named pAJ 319.

Further, by introducing pAJ 319 into B-5 strain defficient for the β subunit of TS (hereafter simply referred to as TSB), tryptophan auxotropy disappeared similarly as described above, whereby it was clarified that trp A and trp B genes were present on the 3.0 Kb fragment inserted at the pst I site of pAJ 1844.

(6) TS activity of transformant:

A specimen strain was cultured in 20 ml of medium for L-tryptophan production (described hereinafter). From the cultured cells, a lysate was prepared by an ultrasonic wave treatment and centrifuged at 32,000×g for 30 minutes to obtain the supernatant. The supernatant was used as a crude enzyme solution. Using an enzyme reaction solution (1 ml in total amount) consisting of 100 mM tris hydrochloride buffer (pH 7.8), 0.4 mM indole, 30 mM L-serine, 40 μm pyridoxal-5'-phosphate and 180 mM sodium chloride, TSB activity was measured. The reaction was carried out at 30° C. for 30 minutes, 0.1 ml of 1N NaOH was added, the remaining indole was extracted with toluene, color was then formed by an indole reagent and then the color was measured by a spectrophotometer (at 540 mn). The results are shown in Table 1.

It was observed that the specific activity of Ts of the transformant AJ 12139 (FERM-P7750, FERM-BP 847) became about 11 times larger than that of the wild strain (AJ 12036) (FERM-P7559, FERM-BP 734) and it was confirmed that the TS activity of the transformant was inhibited only slightly even in the presence of 20 mM L-tryptophan.

TABLE 1

| | TS activity (amount of decreased indole in mole/min/mg amount of protein) | |
|---|---|---|
| | Amount of L-Tryptophan Added | |
| Strain | 0 mM | 20 mM |
| AJ 12139 | 81.0 (100) | 66.4 (82) |
| AJ 12036 | 7.1 (100) | 4.6 (65) |

(7) L-tryptophan Productivity of transformant:

From the AJ 12139 strain desribed above, recombinant plasmid pAT 319 was extracted by the process of (2) and introduced into L-tryptophan-producing strain M-274, which was derived from AJ 12036 strain as a 5-fluorotryptophan-resistant strain by the transformation process described in (4). Transformants were selected which were chloramphenicol resistant.

The thus obtained transformants named AJ 12140 and M-274 were cultured and L-tryptophan productivity was examined. The results are shown in Table 2. The cultivation was performed by inoculating specimen strains in 3 ml of a medium in test tubes or 20 ml in shoulder-equipped flasks. The medium contained 130 g of glucose, 25 g of $(NH_4)_2SO_4$, 12 g of fumaric acid, 3 g of acetic acid, 1 g of $KH_2PO_4$, 8 mg of $MgSO_4.4H_2O$, 1 μg of $MgSO_4.7H_2O$. 50 μg of biotin, 2000 μg of thiamine hydrochloride, 650 mg of tryosine, 400 mg of DL-methionine and 50 g of $CaCO_3$ in 1 liter of water. Shaking was carried out at 30° C. for 72 hours. After culturing. L-tryptophan in the supernatant was quantitatively assayed by microbioassay. (See Table 2.)

TABLE 2

| Strain | Amount of L-Tryptophan accumulated (g/l) |
|---|---|
| AJ 12140 | 5.0 |
| M-274 | 1.6 |

EXAMPLE 2

(1) Introduction of pAJ 319 into bacteria belonging to the genus Corynebacterium pAJ 319 plasmid was introduced into *Corynebacterium glutamicum* wild strain AJ 11560 (FERM-P 5485) in a manner similar to Example 1. Selection was made by chloramphenicol resistance to obtain transformant AJ 12141 (FERM-P7748, FERM-BP 845). It was confirmed by agarose gel electrophoresis that the strain possessed pAJ319.

(2) L-Tryptophan productivity of transformant:

Transformant AJ 12141 (FERM-P7748) was cultured under the culture conditions as in Example 1. The results are shown in Table 3. The aqueous medium contained in 1 liter 100 g of glucose, 40 g of $(NH_4)_2SO_4$, 1 g of $KH_2PO_4$, 0.4 g of $MgSO_4.7H_2O$, 2 ppm of $Mn^{2+}$, 300 μg of biotin, 200 μg of thiamine hydrochloride, 1 g of Casamino acid, 10 ml of Aji-eki and 50 g of CaCO₃ and the pH was 7.2. (See Table 3.)

TABLE 3

| Strain | Amount of L-Tryptophan accumulated (g/l) |
|---|---|
| AJ 12141 | 0.2 |
| AJ 11560 | 0 |

EXAMPLE 3

AJ 12140 and AJ 12141 obtained in Examples 1 and 2, respectively, were cultured in a medium supplemented with anthranilic acid or indole. The results are shown in Table 4. Culture conditions were the same as in Example 1 part (7). Anthranilic acid was added in an amount of 0.5% after 48 hours from the initiation of the culture. On the other hand, indole was fed in portions in a total amount of 0.5% during 48 to 72 hours. For controls, host strains M-274 and AJ 11560 used in Examples 1 and 2 were cultured under the same condition. Further, the result obtained by culturing each strain in a medium supplemented with neither anthranilic acid nor indole are also shown in Table 4:

TABLE 4

| | Amount of L-tryptophan accumulated (g/l) | | |
|---|---|---|---|
| Strain | With added anthranilic acid | With added indole | No addition |
| AJ 12140 | 6.3 | 7.0 | 4.8 |
| M-247 | 1.8 | 2.0 | 1.6 |
| AJ 12141 | 0.4 | 0.5 | 0.2 |
| AJ 11560 | 0.1 | 0.1 | 0 |

One platinum loop volume of bacterial cells shown in Table 5 was inoculated in 50 ml of CMG medium charged in a 50 ml flask equipped with shoulder followed by culturing at 30° C. for 20 hours. Chloramphenicol (10 μg/ml) was added for AJ 12140 and AJ 12141. Cells were collected by centrifuging 1 liter of the culture broth and resuspended in 1 liter of 0.1% NH₄Cl-NH₄OH buffer (pH 8.0) containing 20 g of anthranilic acid and 20 g of 5-phosphoribosyl pyrophosphate. The mixture was shaken at 37° C. for 20 hours. The amount of L-tryptophan accumulated is shown in Table 5.

TABLE 5

| Strain | Amount of L-Tryptophan accumulated (g/l) |
|---|---|
| AJ 12140 | 6.0 |
| M-247 | 3.0 |
| AJ 12141 | 1.5 |
| AJ 11560 | 0.5 |

EXAMPLE 5

Both strain AJ 12140 and AJ 12141 shown in Table 6 were cultured under the same culture conditions as in Example 4. Cells were collected by centrifuging 1 liter of the culture broth and were resuspended in 100 ml of a reaction mixture shown in Table 6 having a composition of 0.1 g/dl of Na₂SO₃, 0.3 g/dl of DETA, 0.01 g/dl of pyridoxal phosphate and 5.4 g/dl of inosine (pH 8.5) as basic ingredients. The suspension was reacted at 30° C. for 8 hours. The results are shown in Table 6.

TABLE 6

| Substrate | Concentration in reaction solution (M) | | |
|---|---|---|---|
| Indole | 0.2 | 0.2 | 0.2 |
| L-Serine | 0.2 | 0 | 0 |
| Pyruvic acid | 0 | 0.2 | 0 |
| β-DL-Chloroalanine | 0 | 0 | 0.2 |
| Strain | L-tryptophan accumulation | | |
| AJ 12140 | 0.14 | 0.04 | 0.02 |
| AJ 12141 | 0.06 | 0.02 | 0.01 |

Plasmid pAJ 1844 used as a vector in the present invention was deposited in the Institute of Microorganism Technology in the form introduced in *Escherichia coli* AJ 11883 (FERM-P 6518, FERM-BP 137), and can be purified by growing AJ 11883 strain to reach the late exponential growth phase then lysing with lysozyme and SDS, centrifuging at 30,000×g, adding polyethylene glycol to the resulting supernatant and fractionating the precipitated DNA by cesium chlorideethidium bromide equilibrium density gradient centrifugation.

Further, No. 21 strain and -247 strain used in Example 1 can be obtained from AJ 12139 and AJ 12140, respectively, by eliminating composite plasmide in host cells without impairing the host cells according to the following technique. Plasmids may be spontaneously lost from the host or may be eliminated by a "removal" operation (Bact. Rev., 36, p. 361–405 (1972)). An example of the removal operation is as follows: a small amount of a strain is inoculated on a medium containing acridine orange in such a concentration (2–50 μg/ml) as to incompletely inhibit growth of the host, in a cell count of about 10⁴ cells per ml to incompletely inhibit the growth of the host bacteria. Then, overnight cultivation is carried out at 27° C. to 35° C. (J. Bacteriol., 88, 261 (1964)). The culture solution is spread on agar medium and then cultured at 27° C. to 42° C. overnight. Among colonies appearing on the medium, the desired one from which plasmids are removed, is that which has lost chloramphenicol resistance.

In addition, No. 21 strain and M-247 strain may be obtained from AJ 12139 and AJ 12140, respectively, by the following technique. Namely, each transformant deposited is subcultured on a CMG plate several times, and separated colonies are examined by a chloramphenicol resistance test on chloramphenicol-sensitive colonies. The existence of a plasmid is examined by the process described in Example 2, part (2). A strain having no plasmid is either No. 21 strain or M-247 strain.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A process for producing L-tryptophan, which comprises:
    contacting in a medium a Coryneform bacterium capable of producing L-tryptophan, wherein said bacterium is Brevibacterium lactofermentum FERM BP-846 or Corynebacterium glutamicum FERM BP-845m with raw material capable of being enzymatically converted into L-tryptophan, wherein said bacterium contains recombinant DNA constructed by connecting a feedback resistant gene coding for tryptophan synthase in a mutant strain of B. lactofermentum with a plasmid vector capable of proliferating in said Coryneform bacterium, allowing L-tryptophan to accumulate in said medium, and isolating L-tryptophan.

2. A process for producing L-tryptophan, which comprises:

contacting in a medium a Coryneform bacterium capable of producing L-tryptophan, wherein said bacterium is *Brevibacterium lactofermentum* FERM BP-847, with a raw material capable of being enzymatically converted into L-tryptophan, wherein said bacterium contains recombinant DNA constructed by connecting a feedback resistant gene coding for tryptophan synthase in a mutant strain of *B. lactofermentum* with a plasmid vector capable of proliferating in said Coryneform bacterium, allowing L-tryptophan to accumulate in said medium, and isolating L-tryptophan.

3. The process of claim 1 or 2, wherein said raw material is anthranilic acid or indole.

4. The process of claim 1 or 2, wherein when said Coryneform bacterium is contacted with said raw material, said Coryneform bacterium is in the form of a culture broth, an immobilized cell, or a proteinaceous fraction obtained from said bacterium.

5. The process of claim 1, wherein said raw material is a carbohydrate.

6. The process of claim 1 or 2, wherein inosine is added to said medium whereby as tryptophan is formed, a tryptophan-inosine complex forms which is substantially insoluble in said medium.

7. The process of claim 3, wherein when anthranilic acid is used as said raw material, a ribose donor selected from the group consisting of ribose, 5-phosphoribose, 1-phosphoribose, and 5-phosphoribose pyrophosphate is added to said medium.

8. The process of claim 3, wherein when indole is used as said raw material, an alanine side chain donor or pyruvic acid, and ammonium ion are added to said medium.

9. The process of claim 8, wherein said alanine side chain donor is represented by the formula:

$$X-CH_2-CH(NH_2)CO_2H$$

wherein X is hydroxyl, halogen, an alkyl mercapto group, a mercapto group, an alkoxy group, a benzyloxy or a thiobenzyl group.

* * * * *